(12) United States Patent
Pruche et al.

(10) Patent No.: US 7,704,285 B2
(45) Date of Patent: Apr. 27, 2010

(54) COMPOSITION FOR COLORING A KERATIN MATERIAL, COMPRISING AT LEAST TWO COMPONENTS, AND COLORING PROCESSES

(75) Inventors: Francis Pruche, Senlis (FR); Véronique Chevalier, Villecresnes (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/558,352

(22) Filed: Sep. 11, 2009

(65) Prior Publication Data

US 2010/0005599 A1 Jan. 14, 2010

Related U.S. Application Data

(62) Division of application No. 10/718,683, filed on Nov. 24, 2003, now abandoned.

(60) Provisional application No. 60/507,119, filed on Oct. 1, 2003.

(30) Foreign Application Priority Data

Nov. 29, 2002 (FR) .................................. 02 15051

(51) Int. Cl.
*A61Q 5/10* (2006.01)
(52) U.S. Cl. ...................... 8/405; 8/424; 8/628; 8/629; 132/202; 132/208
(58) Field of Classification Search .................. 8/405, 8/424, 628, 629; 132/202, 208
See application file for complete search history.

(56) References Cited

U.S. PATENT DOCUMENTS

| 4,226,784 A | 10/1980 | Kalopissis et al. |
| 5,895,642 A | 4/1999 | Sanders et al. |
| 6,399,046 B1 | 6/2002 | Schönrock et al. |
| 6,723,136 B2 | 4/2004 | Pruche |
| 6,736,861 B2 | 5/2004 | Patel et al. |
| 6,953,486 B2 | 10/2005 | Pruche |
| 2002/0124330 A1 | 9/2002 | Pruche |
| 2003/0163878 A1 * | 9/2003 | Pruche .................. 8/408 |

FOREIGN PATENT DOCUMENTS

| EP | 0 621 029 | 10/1994 |
| JP | 11-92347 | 4/1999 |
| JP | 2002-332222 | 11/2002 |
| WO | WO 92/20321 | 11/1992 |
| WO | WO 92/20354 | 11/1992 |
| WO | WO 02/30371 | 4/2002 |
| WO | WO 02/30375 | 4/2002 |

OTHER PUBLICATIONS

English language Derwent abstract of JP 11-92347, (1994).
English language Derwent abstract of JP 2002-332222.
English language abstract of WO 02/30371, (2002).
English language abstract of WO 02/30375, (2002).
French Search Report for FR 02 15051 (priority application for U.S. Appl. No. 10/718,683) dated Aug. 8, 2003.
K. Schallreuter, "In Vivo In Vitro Evidence for Hydrogen Peroxide ($H_2O_2$) Accumulation in the Epidermis of Patients with Vitiligo and its Successful Removal by a UVB-Activated Pseudocatalase"; J Investing Dermator Symp Proc Sep; 451; 91-96 (1999).

* cited by examiner

*Primary Examiner*—Eisa B Elhilo
(74) *Attorney, Agent, or Firm*—Finnegan, Henderson, Farabow, Garrett & Dunner, LLP

(57) ABSTRACT

Processes for coloring a keratin material, comprising applying to the keratin material, in the presence of oxygen, at least one component (A) comprising, in a physiologically acceptable medium:—at least one dye precursor chosen from compounds comprising at least one aromatic ring comprising at least two hydroxyl groups borne by two successive carbon atoms of the at least one aromatic ring, and at least one catalytic system comprising at least one first catalyst (1) chosen from Mn(II) and Zn(II) salts and oxides and/or at least one second catalyst (2) chosen from alkali metal hydrogen carbonates and alkaline-earth metal hydrogen carbonates followed by applying at least one component (B) comprising at least one acidic composition to fix the shade and followed by applying at least one component (C) comprising at least one alkaline composition to increase the intensity of the color or to modify the shade and optionally fixing the new color or shade obtained by applying a new application of at least one composition (B).

63 Claims, No Drawings

COMPOSITION FOR COLORING A KERATIN MATERIAL, COMPRISING AT LEAST TWO COMPONENTS, AND COLORING PROCESSES

This is a divisional of application Ser. No. 10/718,683, filed Nov. 24, 2003, now abandoned which claims benefit of priority of U.S. Provisional Application No. 60/507,119, filed Oct. 1, 2003 and French Patent Application No. 02 15051, filed Nov. 29, 2002, all of which are incorporated herein by reference.

Disclosed herein is a composition for coloring a keratin material, wherein the composition comprises at least two components, and can be used, for example, for coloring human skin and/or keratin fibres. Also disclosed herein are various coloring processes using the inventive composition.

In the field of coloring a human keratin material, such as skin, hair, eyelashes, eyebrows and body hair, enzymatic catalysts are known and can be used to activate the coloration of dye precursors. Thus, the coloration of polyphenols can be activated by oxidation in the presence of natural polyphenol oxidase. For example, catechin, in the presence of natural polyphenol oxidase, can give an orange-yellow coloration and dihydroxyphenylalanines (L-DOPA) can give melanin. At least one advantage of these enzymatic catalysts includes the production of pigments with novel colors and shades, without using oxidizing compounds. However, at least one drawback of this coloring process is the use of enzymes, for which the toxicological risks, the stability in compositions, the reproducibility, the price, and the immobilization often required can be factors that greatly limit their uses.

Moreover, these catalysts can be of a protein nature and the use of proteins is not without risk for cosmetological or dermatological use, for example, on account of sensitization reactions.

The use of enzymatic catalysts in cosmetic preparations such as self-tanning products may not always allow a uniform coloration of the skin. Applying compositions comprising dihydroxyacetone (or DHA), which is typically used in this type of application, to the whole body can be long and tedious, and it may be difficult to obtain a uniform coloration.

In the field of tanning and self-tanning creams, an improvement has been obtained by using chemical catalysts instead of enzymatic catalysts. Thus, Patent Application No. WO 92/20321 A describes a cream that can promote the tanning of fair skin when exposed to sunlight or to UVB rays, the composition of which comprises a physiologically acceptable medium and a pseudocatalase. The pseudocatalase is a coordination complex of a transition metal, the metal of which is Cu(I), Fe(II) or Mn(II) and the ligand of which is bicarbonate. The term "pseudocatalase" means a physiologically acceptable compound that catalyses the dismutation of $H_2O_2$ in vivo in a manner analogous to a catalase.

To treat skin depigmentation associated with blockages of the conversion of tyrosine to melanin, for example, vitiligo, Patent Application No. WO 92/20354 and U.S. Pat. No. 5,895,642 describe compositions comprising a pseudocatalase in a physiologically acceptable medium. This pseudocatalase is a coordination complex of Fe(II), Cu(I) or Mn(II), the ligand being bicarbonate.

The article by K. Schallreuter ("Pseudocatalase is a Bis-Manganese III-EDTA-$(HCO_3)_2$ Complex Activated by UVB or Natural Sun; J Investing Dermator Symp Proc 1999 September; 451; 91-6) discloses the use of a mixture of sodium hydrogen carbonate and manganese that has pseudocatalase activity, for the treatment of vitiligo. However, there is no disclosure regarding coloration in any of these documents. Moreover, this composition contains EDTA, a chelating agent.

In the field of coloring the hair, European Patent No. EP 621 029 describes a composition comprising sodium chlorite, a water-soluble Fe, Mn or Cu salt, or a chelate of this salt, and an oxidation dye precursor. Coloring the hair requires the use of $H_2O_2$-ammonium or amine combinations.

A process for intensifying the natural tanning of the skin is also known in U.S. Pat. No. 6,399,046; this process comprises stimulating melanogenesis in situ with polyphenols of the type such as catechin, catechin gallic ester or plant extracts comprising catechin or a catechin gallic ester, for example, extracts of green tea leaf. This process may not afford direct and fast coloration on the skin and the presence of melanocytes may be necessary.

Patent Application No. WO 02/30371 also discloses agents for coloring a keratin material, comprising at least one propigmenting enzyme, and an amino acid comprising a thiol group in the presence of oxygen, via oxidation by means of a purely chemical catalytic system comprising at least one first constituent chosen from Mn(II) and Zn(II) salts and oxides, and at least one second constituent chosen from alkali metal hydrogen carbonates and alkaline-earth metal hydrogen carbonates.

There is thus a need to find novel compositions for coloring a keratin material, for example, for coloring the skin and/or keratin fibres, which does not require the use of enzymatic systems.

It was discovered in Patent Application No. WO 02/30375 that it is possible to achieve this aim by using a coloring agent (A) comprising at least one dye precursor chosen from compounds comprising at least one aromatic ring comprising at least two hydroxyl groups (OH) borne by two consecutive carbon atoms of the at least one aromatic ring and optionally an amino acid comprising a thiol group, capable of becoming colored in the presence of oxygen, via oxidation by means of a purely chemical catalytic system comprising at least one first constituent chosen from Mn(II) and Zn(II) salts and oxides, and at least one second constituent chosen from alkali metal hydrogen carbonates and alkaline-earth metal hydrogen carbonates. The chemical catalytic system behaves like a pseudo-oxidase which is capable of imitating the oxidase activity without the drawbacks associated with the use of an enzymatic system.

However, the present inventors have found, first, that the persistence over time, the intensity and the uniformity of the colors obtained with this type of coloring agent (A) can be further improved. Second, this type of process may not allow sufficient control of the coloration reaction on the hair or the skin and may not produce a wide range of shades that are more or less intense depending on the needs of the user, for example, at different times of the day or over a period of several days.

The present inventors have discovered, surprisingly, that by applying to a keratin material to be colored an acidic composition (B) after the application of the coloring agent component (A) as defined above, the coloring reaction revealed by the agent (A) can be stopped. Via a mordanting phenomenon, the acidic composition (B) allows the tannins thus formed to be fixed onto the proteins of the keratin material. The application of the acidic composition (B) can make it possible, unexpectedly, first, to reinforce the fastness of the color over time and second to control the coloration reaction on the keratin material by stopping it when the shade desired by the user is obtained.

The present inventors have also discovered, surprisingly, that by applying an alkaline composition (C) after the application of the coloring agent component (A) as defined above and optionally after applying the acidic composition (B) defined above, the color obtained in the preceding step can be revived by increasing its intensity; the new shade obtained can again be controlled by stopping the reaction at the chosen moment by applying the composition (B).

This process of coloring, fixing and/or reviving the color may be repeated as many times as necessary, over a period of several days.

Disclosed herein is thus a coloring composition for a keratin material, comprising,
(i) at least one coloring agent component comprising, in a physiologically acceptable medium,
at least one dye precursor chosen from compounds comprising at least one aromatic ring comprising at least two hydroxyl groups borne by two successive carbon atoms of the at least one aromatic ring, and
at least one catalytic system comprising at least one first catalyst (1) chosen from Mn(II) and Zn(II) salts and oxides and at least one second catalyst (2) chosen from alkali metal hydrogen carbonates and alkaline-earth metal hydrogen carbonates;
wherein the catalysts (1) and (2) are present with the at least one dye precursor in a single composition (A) or separated into two components ($A_1$) and ($A_2$) wherein the at least one dye precursor is present in at least one of the components ($A_1$) and ($A_2$);
and at least one component chosen from:
(ii) a component (B) comprising at least one acidic composition, and
(iii) a component (C) comprising at least one alkaline composition.

Further disclosed herein are various processes for coloring a keratin material using the coloring composition.

Even further disclosed herein are packaging and presentation forms for the various components of the disclosed coloring composition.

The term "keratin material" means natural textile fibres comprising keratin, for example, cotton, silk, wool, and materials such as skin, scalp, nails, hair, body hair, eyelashes and eyebrows, and also mucous membranes.

The at least one coloring agent component disclosed herein may be present either as a single composition (A) or as a composition comprising two separate components ($A_1$) and ($A_2$). The at least one coloring agent component comprises at least one dye precursor chosen from compounds comprising at least one aromatic ring comprising at least two hydroxyl groups borne by two consecutive carbon atoms of the at least one aromatic ring and at least one catalytic system comprising at least one first catalyst (1) chosen from Mn(II) and Zn(II) salts and oxides and at least one second catalyst (2) chosen from alkali metal hydrogen carbonates and alkaline-earth metal hydrogen carbonates; the catalysts (1) and (2) possibly being present in a single composition (A) or separated into two components ($A_1$) and ($A_2$).

For example, the at least one coloring agent component, comprising the two components ($A_1$) and ($A_2$), may be packaged separately, with:
($A_1$) comprising, in a physiologically acceptable medium, the at least one dye precursor and one of the catalysts (1) or (2) and ($A_2$) comprising, in a physiologically acceptable medium, the other catalyst (1) or (2) not present in the component ($A_1$).

The proportions of the at least one first catalyst (1) to the at least one second catalyst (2) may, for example, be chosen such that:

$$\frac{[Mn(II)]}{[HCO_3]} \leq 1 \text{ with } [Mn(II)] \neq 0$$

$$\frac{[Zn(II)]}{[HCO_3]} \leq 1 \text{ with } [Zn(II)] \neq 0$$

$$\frac{[Mn(II) + Zn(II)]}{[HCO_3]} \leq 1 \text{ with } [Mn(II)] \text{ and } [Zn(II)] \neq 0$$

wherein [Mn(II)], [Zn(II)] and [$HCO_3$] represent, respectively, the molar concentrations of Mn(II), Zn(II) and $HCO_3$ in the composition.

For example, the ratio $$\frac{[Mn(II)]}{[HCO_3]}$$

can range from $10^{-5}$ to $10^{-1}$, further, for example, from $10^{-3}$ to $10^{-2}$ and, even further, for example, can be about $5 \times 10^{-3}$.

In the case of Zn(II), the ratio $$\frac{[Zn(II)]}{[HCO_3]}$$

can range, for example, from 10 to 100 times greater than the ratio $$\frac{[Mn(II)]}{[HCO_3]}.$$

For example, this ratio can be $10^{-4}$ or more, further, for example, $10^{-3}$ or more and, even further, for example, about $5 \times 10^{-1}$.

In the case of a mixture of Mn(II) and Zn(II), the ratio $$\frac{[Mn(II) + Zn(II)]}{[HCO_3]}$$

may, for example, range from $10^{-5}$ to $10^{-1}$ and, further, for example, from $10^{-3}$ to $10^{-2}$, this ratio being chosen higher when the proportion of Zn(II) in the mixture increases.

For example, the molar concentration of Mn(II), Zn(II) or Mn(II)+Zn(II) in the final composition can range, for example, from $10^{-3}$ to 10 mM/l and, further, for example, from $10^{-2}$ to 1 mM/l.

When only Mn(II) salt(s) and/or oxide(s) are used, the molar concentration of Mn(II) in the final composition can, for example, range from $10^{-3}$ to $10^{-1}$ mM/l and further, for example, from $10^{-2}$ to $10^{-1}$ mM/l.

For example, when only Zn(II) salt(s) and/or oxide(s) are used, the concentration of Zn(II) in the final composition can range from $5 \times 10^{-2}$ to 10 mM/l and further, for example, from $5 \times 10^{-1}$ to 1 mM/l.

For example, the Mn(II) and Zn(II) salts that can be used in the coloring agent disclosed herein may be chosen from at least one of chloride, fluoride, iodide, sulphate, phosphate, nitrate and perchlorate, and carboxylic acid salts. The Mn(II) and Zn(II) salts may be derived from natural mineral water.

For example, the Mn(II) salts may be chosen from manganese chloride, manganese carbonate, such as rhodochrosite, Mn(II) difluoride, Mn(II) acetate tetrahydrate, Mn(II) lactate trihydrate, Mn(II) phosphate, Mn(II) iodide, Mn(II) nitrate trihydrate, Mn(II) bromide, Mn(II) perchlorate tetrahydrate and Mn(II) sulphate monohydrate.

In one embodiment, $MnCl_2$ and $ZnCl_2$ salts can be used.

The carboxylic acid salts can, for example, be chosen from hydroxylated carboxylic acid salts such as gluconate.

The alkali metal and alkaline-earth metal hydrogen carbonates used in the coloring agent disclosed herein may, for example, be chosen from at least one of Na, K, Mg, Ca hydrogen carbonate, for example, Na hydrogen carbonate. The alkali metal and alkaline-earth metal hydrogen carbonates may be derived from natural mineral water.

As discussed herein, the at least one catalytic system disclosed herein constitutes a pseudo-oxidase in that it oxidizes polyphenols, in the presence of oxygen, as would a natural enzymatic catalyst having polyphenol oxidase activity.

The at least one dye precursor disclosed herein is chosen from compounds comprising at least one aromatic ring, such as a benzene ring, comprising at least two hydroxyl groups (OH) borne by two consecutive carbon atoms of the at least one aromatic ring.

The at least one aromatic ring may, for example, be chosen from fused aromatic rings optionally comprising at least one hetero atom, such as naphthalene, tetrahydronaphthalene, indane, indene, anthracene, phenanthrene, indole, isoindole, indoline, isoindoline, benzofuran, dihydrobenzofuran, chroman, isochroman, chromene, isochromene, quinoline, tetrahydroquinoline and isoquinoline.

The at least one dye precursor disclosed herein may be chosen from compounds of formula (I):

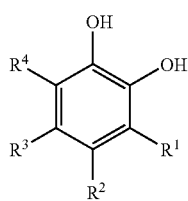

(I)

wherein:
$R^1$, $R^2$, $R^3$, and $R^4$, which may be identical or different, are each chosen from a hydrogen atom, halogen atoms, hydroxyl groups, carboxyl groups, alkylcarboxylate groups, optionally substituted amino groups, optionally substituted linear and branched alkyl groups, optionally substituted linear and branched alkenyl groups, optionally substituted cycloalkyl, alkoxy, alkoxyalkyl and alkoxyaryl radicals, the aryl group being optionally substituted, aryl and substituted aryl radicals, optionally substituted heterocyclic radicals, and radicals comprising at least one silicon atom, wherein two of the substituents chosen from $R^1$, $R^2$, $R^3$, and $R^4$ together form at least one ring chosen from saturated and unsaturated rings optionally comprising at least one hetero atom and optionally fused with at least one ring chosen from saturated and unsaturated rings optionally comprising at least one hetero atom.

The saturated and unsaturated, optionally fused rings may also be optionally substituted.

The alkyl radicals may, for example, be chosen from $C_1$-$C_{10}$ alkyl radicals and, for example, $C_1$-$C_6$ alkyl radicals, such as methyl, ethyl, propyl, butyl, pentyl and hexyl radicals.

The alkoxy radicals may, for example, be chosen from $C_1$-$C_{10}$ alkoxy radicals, such as methoxy, ethoxy, propoxy and butoxy radicals.

The alkoxyalkyl radicals may, for example, be chosen from ($C_1$-$C_{20}$)alkoxy($C_1$-$C_{20}$)alkyl radicals, such as methoxymethyl, ethoxymethyl, methoxyethyl, ethoxyethyl radicals, etc.

The cycloalkyl radicals may, for example, be chosen from $C_4$-$C_8$ cycloalkyl radicals, such as cyclopentyl and cyclohexyl radicals. The cycloalkyl radicals may be substituted cycloalkyl radicals, for example, substituted with at least one group chosen from alkyl, alkoxy, carboxylic acid, hydroxyl, amine and ketone groups.

The alkenyl radicals may, for example, be chosen from $C_1$-$C_{20}$ radicals, such as ethylene, propylene, butylene, pentylene, methyl-2-propylene and decylene radicals.

The radicals comprising at least one silicon atom may, for example, be chosen from polydimethylsiloxane, polydiphenylsiloxane, polydimethylphenylsiloxane and stearoxydimethicone radicals.

The heterocyclic radicals may, for example, be chosen from radicals comprising at least one hetero atom, such as O, N and S. For example, in one embodiment the at least one hetero atom may be O or N. The heterocyclic radicals may, for example, be optionally substituted with at least one group chosen from alkyl, alkoxy, carboxylic acid, hydroxyl, amine and ketone groups.

The heterocyclic radicals may, for example, be chosen from furyl, pyranyl, pyrrolyl, imidazolyl, pyrazolyl, pyridyl and thienyl radicals.

Further, for example, the heterocyclic radicals may be chosen from fused groups such as benzofuryl, chromenyl, xanthenyl, indolyl, isoindolyl, quinolyl, isoquinolyl, chromanyl, isochromanyl indolinyl, isoindolinyl, coumarinyl and isocoumarinyl groups, these groups possibly being substituted, for example, with at least one OH group.

The at least one dye precursor may, for example, be chosen from:
flavanols such as catechin and epicatechin gallate,
flavonols such as quercetin,
anthocyanidins such as peonidin,
anthocyanins, for example oenin,
hydroxybenzoates, for example gallic acid,
flavones such as luteolin, and
iridoids such as oleuropein, these products possibly being osylated (for example glucosylated) and/or in the form of oligomers (procyanidins);
hydroxystilbenes, for example 3,3',4,5'-tetrahydroxystilbene, which may be optionally osylated (for example glycosylated);
3,4-dihydroxyphenylalanine and derivatives thereof;
2,3-dihydroxyphenylalanine and derivatives thereof;
4,5-dihydroxyphenylalanine and derivatives thereof;
4,5-dihydroxyindole and derivatives thereof;
5,6-dihydroxyindole and derivatives thereof;
6,7-dihydroxyindole and derivatives thereof;
2,3-dihydroxyindole and derivatives thereof;
dihydroxycinnamates such as caffeic acid and chlorogenic acid;
hydroxycoumarins;
hydroxyisocoumarins;
hydroxycoumarones;

hydroxyisocoumarones;
hydroxychalcones;
hydroxychromones;
anthocyans;
quinones; and
hydroxyxanthones.

When the at least one dye precursor has D and L forms, these two forms may also be used in the compositions disclosed herein.

By varying the nature of the at least one dye precursor and its proportion in the composition, the color of the final coloring composition may be varied. A range of colors can thus be obtained.

The polymers formed, for example, with catechin, gallic acid and derivatives thereof (tannins) have antimicrobial properties by trapping microorganisms during polymerization. These tannins may also have astringent properties that may be advantageous for the skin.

The at least one dye precursor may, for example, be chosen from extracts of plants, of fruits, of citrus plants and of vegetables, which contain many polyphenols as defined above.

The plant extracts may, for example, be chosen from extracts of rose, of sorghum and of tea.

The fruit extracts may, for example, be chosen from extracts of apple; of grape, such as grapeseed; of cocoa, such as beans and/or pods; and of banana.

The vegetable extracts may, for example, be extracts of potato.

It is also possible to use mixtures of plant and/or fruit extracts such as mixtures of extracts of apple and of tea and mixtures of extracts of grape and of apple.

Depending on the parts of the fruits used, for example, grape pulp or seed, the coloration obtained may be different.

The amount of the at least one dye precursor in the final composition should be sufficient to obtain a visible coloration. This amount may vary within a wide range depending on the nature of the at least one dye precursor and the desired intensity for the coloration.

In general, a suitable coloration will be obtained when the amount of the at least one dye precursor is such that the content of the at least one dye precursor in the final coloring agent component is at least 10 micromol per millilitre of the coloring agent component.

The physiologically acceptable medium for the coloring agent component can be a solid or liquid medium that does not harm the coloring property of the precursors or the catalytic effect of the catalytic system. It may, for example, be a solubilizing medium for the at least one dye precursor and have bacteriostatic properties.

At least one solvent for the at least one dye precursor, suitable for formulating the compositions disclosed herein, may, for example, be chosen from water, alcohols and polar solvents.

The alcohols may, for example, be chosen from lower ($C_1$-$C_6$) alkanols such as ethanol and isopropanol, and alkanediols such as ethylene glycol, propylene glycol and pentanediol.

The polar solvents may, for example, be chosen from at least one of ethers; esters, such as acetates; dimethyl sulphoxide (DMSO); N-methylpyrrolidone (NMP); and ketones, such as acetone.

The physiologically acceptable medium may, for example, comprise water, such as distilled or deionized water; or a water/alcohol mixture, such as water/ethanol.

The amount of alcohol in the water/alcohol mixture may, for example, range from 80% by weight, relative to the total weight of the water/alcohol mixture, further, for example, from 1% to 50% by weight, relative to the total weight of the water/alcohol mixture, and further, for example, from 5% to 20% by weight, relative to the total weight of the water/alcohol mixture.

In one embodiment, the at least one coloring agent component disclosed herein is free of an agent for chelating the Mn(II) and/or Zn(II) salts used, since these agents tend to inhibit the oxidation of the dye precursors.

In another embodiment, the at least one coloring agent component disclosed herein comprises no propigmenting enzyme.

The at least one solvent may be present in an amount ranging, for example, from 1% to 40% by weight, relative to the total weight of the coloring agent component, and further, for example, ranging from 5% to 30% by weight, relative to the total weight of the coloring agent component.

When it is intended for coloring the hair, the at least one coloring agent component in the form of a single composition (A) or a composition comprising two separate components ($A_1$) and ($A_2$) packaged separately may be in various forms. For example, the at least one coloring agent component can be provided in a form chosen from lotions, creams, gels, and any other forms that are suitable for coloring keratin fibres, for example, human hair.

The at least one coloring agent component may also comprise at least one adjuvant conventionally used in hair coloring compositions. For example, the at least one adjuvant may be chosen from anionic, cationic, nonionic, amphoteric and zwitterionic surfactants; anionic, cationic, nonionic, amphoteric and zwitterionic polymers; mineral and organic thickeners, such as, anionic, cationic, nonionic and amphoteric polymeric associative thickeners; antioxidants; penetrating agents; fragrances; buffers; dispersants; conditioners; for example, volatile and non-volatile, modified and unmodified silicones; film-forming agents; ceramides; opacifiers; and propellants.

When it is intended for coloring the skin, the at least one coloring agent component in the form of a single composition (A) or a composition comprising two separate components ($A_1$) and ($A_2$) packaged separately may be provided in a form chosen from creams and milks, gels and cream-gels, lotions, powders and solids, and any other forms suitable for coloring the skin.

The at least one coloring agent component may also comprise at least one adjuvant conventionally used in skin coloring compositions. For example, the at least one adjuvant may be chosen from fatty substances; organic solvents; anionic, cationic, nonionic, amphoteric and zwitterionic surfactants; anionic, cationic, nonionic, amphoteric and zwitterionic polymers; mineral and organic thickeners, such as anionic, cationic, nonionic and amphoteric polymeric associative thickeners; softeners; antioxidants; free-radical scavengers; opacifiers; emollients; silicones; antifoams; moisturizers; vitamins; insect repellents; fragrances; surfactants; anti-inflammatory agents; substance P antagonists; fillers; propellants; dyes; and organic and mineral sunscreens.

The at least one coloring agent component in the form of a single composition (A) or a composition comprising two separate components ($A_1$) and ($A_2$), which may be identical or different, each may be packaged in various forms, for example, airtight metal tubes, sachets, sealed wipes, ampules, aerosols, sprays, solid blocks, and any other packaging form that is suitable for coloring the chosen keratin material.

In one embodiment, the at least one coloring agent component disclosed herein may be packaged in a one-compartment device comprising the at least one dye precursor and the at least one catalytic system.

This device may, for example, be in a form chosen from airtight metal tubes; sachets; sealed wipes; ampules; aerosols comprising at least one standard inert propellent gas chosen from nitrogen, saturated hydrocarbons such as butane, propane and isopropane, and fluorohydrocarbons, for example, Freon®; sprays equipped with a pump without air intake; and solid blocks such as a bead for the bath.

In another embodiment, the at least one coloring agent component disclosed herein may be packaged in the form of a kit comprising two separate containers comprising, respectively, the components ($A_1$) and ($A_2$) as defined herein, the components ($A_1$) and ($A_2$) being mixed together or applied successively at the time of use.

Each of the two containers, which may be identical or different, may be packaged, for example, in a form chosen from airtight tubes, sachets, sealed wipes, ampules, aerosols, sprays equipped with a pump without air intake, solid blocks such as a bath bead, and any other packaging form that is suitable for coloring the chosen keratin material.

A two-compartment aerosol device comprising, respectively, the components ($A_1$) and ($A_2$) and with which a distribution orifice may be selectively placed in communication may also be envisaged; depending on the configuration of the device, the components ($A_1$) and ($A_2$) may be distributed simultaneously or successively at the time of use.

A system comprising two compartments each equipped with a pump without air intake, the first compartment comprising the component ($A_1$) with the at least one dye precursor and one of the catalysts (1) or (2) as defined herein, and the other compartment comprising the component ($A_2$) with the other catalyst (1) or (2) not present in the component ($A_1$), may also be envisaged; depending on the configuration of the device, the components ($A_1$) and ($A_2$) may be distributed simultaneously or successively at the time of use.

In another embodiment, the at least one coloring agent component disclosed herein, present either as a single composition (A) or as a composition comprising two components ($A_1$) and ($A_2$), may be provided in a form of one or two solid blocks that may be disintegrated in water, such as bath beads. The solid blocks may be effervescent.

In the coloring composition disclosed herein, the component (B), the color fixing component, comprises an aqueous composition comprising at least one acid chosen from mineral and organic acids.

The pH of the component (B) may, for example, range from 1 to 6, further, for example, from 2 to 5.

The mineral acids may, for example, be chosen from at least one of hydrochloric acid (HCl) and phosphoric acid ($H_3PO_4$).

The component (B) may comprise naturally acidic water, for example, demineralized water.

The organic acids that may be used in the composition disclosed herein may, for example, be chosen from at least one of acetic acid, α-hydroxy acids, β-hydroxy acids and α- and β-keto acids.

The hydroxy acids may, for example, be chosen from glycolic acid, lactic acid, malic acid, tartaric acid, citric acid, mandelic acid and salicylic acid, and alkyl derivatives thereof, such as 5-n-octanoylsalicylic acid, 5-n-dodecanoylsalicylic acid and 2-hydroxy-3-methylbenzoic acid, and alkoxy derivatives thereof, for example, 2-hydroxy-3-methoxybenzoic acid. The hydroxy acids may, for example, be chosen from at least one of lactic acid, glycolic acid and citric acid.

The component (B) may be packaged in a form chosen from bottles, jars, tubes, sachets, wipes, aerosols, sprays and solid sticks, and any other packaging form that is suitable for coloring the chosen keratin material.

As used herein, the component (C), the component for reviving color, comprises an aqueous composition comprising at least one base chosen from mineral bases and organic bases.

The pH of the component (C) may range, for example, from 7 to 12 and further, for example, from 8 to 10.

The mineral bases used in the composition disclosed herein may, for example, be chosen from at least one of alkali metal and alkaline-earth metal salts, such as sodium hydroxide, potassium hydroxide and aqueous ammonia; alkali metal and alkaline-earth metal hydrogen carbonates such as Na, K, Mg and Ca hydrogen carbonate and, for example, Na hydrogen carbonate. The component (C) may also comprise naturally alkaline mineral water such as Eau de Vichy or Eau de La Roche Posay.

The organic bases may, for example, be chosen from alkanolamines such as triethanolamine.

The component (C) for reviving the color may be packaged in various forms such as bottles, jars, tubes, sachets, wipes, aerosols, sprays and solid sticks, and any other packaging forms that are suitable for coloring the chosen keratin material.

To reveal the coloration of the compositions disclosed herein, it suffices to place the composition comprising at least one dye precursor and an effective amount of the at least one catalytic system disclosed herein in contact with an oxidizing medium such as a medium comprising oxygen, for example, atmospheric oxygen.

The compositions disclosed herein may, for example, be used for coloring the human skin, scalp, nails or keratin fibres such as the hair, the eyelashes, the eyebrows and body hair. Various processes for applying the compositions disclosed herein may be used.

According to a first coloring process, the at least one coloring agent component present as a single composition (A) comprising at least one dye precursor and the at least one catalytic system comprising the at least one catalyst (1) and the at least one catalyst (2) as defined herein is applied to a keratin material, in the presence of oxygen, for example atmospheric oxygen. When the desired shade is obtained, acidic at least one component (B) as defined herein is applied to the keratin material to fix the color. If it is desired to increase the intensity of the color or to modify the shade, alkaline at least one component (C) as defined herein is applied to the keratin material; the new color obtained may be again fixed by means of a new application of the at least one component (B).

According to a second coloring process, the at least one component ($A_1$) comprising at least one dye precursor and one of the catalysts (1) or (2) is applied to the keratin material, and the color is then revealed in the presence of oxygen, for example atmospheric oxygen, by applying the at least one component ($A_2$) comprising the other catalyst (1) or (2) not present in the at least one component ($A_1$). When the desired shade is obtained, the acidic at least one component (B) as defined herein is applied to the keratin material to fix the color. If it is desired to increase the intensity of the color or to modify the shade, the alkaline at least one component (C) as defined herein is applied to the keratin material; the new color obtained may again be fixed by means of a new application of the at least one component (B).

According to a third coloring process, the at least one coloring agent component present as a single composition (A) comprising at least one dye precursor and the at least one catalytic system comprising the at least one catalyst (1) and the at least one catalyst (2) as defined herein is applied to a keratin material, in the presence of oxygen, for example, atmospheric oxygen. If it is desired to increase the intensity of the color or to modify the shade, the alkaline at least one component (C) as defined herein is then applied to the keratin material; the new color obtained may be fixed by applying the at least one component (B) as defined herein.

According to a fourth coloring process, the at least one component ($A_1$) comprising at least one dye precursor and one of the catalysts (1) and (2) is applied to a keratin material, and the color is then revealed in the presence of oxygen, for example atmospheric oxygen, by applying the at least one component ($A_2$) comprising the other catalyst (1) or (2) not present in the at least one component ($A_1$). If it is desired to increase the intensity of the color or to modify the shade, the alkaline component (C) as defined herein is applied to the keratin material; the new color obtained may be fixed by applying the at least one component (B) as defined herein.

Depending on the choice of the at least one dye precursor, the coloring composition disclosed herein may be used in many cosmetic applications. The coloring composition may be used to dye hair.

In the context of skin-specific cosmetics, the coloring composition disclosed herein may be a composition for artificially tanning and/or browning the skin, and/or for giving a healthy complexion.

In the context of skin-specific cosmetics, the coloring composition disclosed herein may be a skin makeup composition, for example, for producing tattoos by means of stencils by adjusting the colors. It may also be used to adjust the color according to the areas of relief of the face. It may be applied to the face or the hands to mask pigmentation defects such as vitiligo or a pregnancy mask, and also skin imperfections such as scars, age marks, chloasma and rosacea.

The coloring composition disclosed herein may be a makeup composition for the nails, the eyelashes and the eyebrows.

The coloring composition disclosed herein may be a composition for coloring keratinous textile fibres. The coloring composition disclosed herein may also be used for coloring food.

The examples that follow illustrate various embodiments disclosed herein, without however, being limiting in nature. In the examples, except where otherwise mentioned, all the percentages and parts are expressed on a weight basis.

EXAMPLE 1

Composition Comprising the Two Components $A_1$ and $A_2$ Below

Component $A_1$: White Cream

| Phase $a_1$: | Glyceryl stearate (and) PEG-100 stearate | 2.5% |
|---|---|---|
| | Polysorbate 60 | 2.5% |
| | Cetyl alcohol | 1% |
| | Stearyl alcohol | 1% |
| | Paraffin | 5% |
| | Preserving agent | 0.1% |
| Phase $b_1$: | Preserving agent | 0.2% |
| | Carbomer | 0.3% |
| | Base | 0.2% |
| | Catechin | 0.2% |
| | Propyl gallate | 2% |
| | $MnCl_2$ | 0.0002% |
| | Water | qs 100% |

Component $A_2$: White Cream

| Phase $a_2$: | Glyceryl stearate (and) PEG-100 stearate | 2.5% |
|---|---|---|
| | Polysorbate 60 | 2.5% |
| | Cetyl alcohol | 1% |
| | Stearyl alcohol | 1% |
| | Paraffin | 5% |
| | Preserving agent | 0.1% |
| Phase $b_1$: | Preserving agent | 0.2% |
| | Carbomer | 0.3% |
| | Sodium bicarbonate | 1% |
| | Base | 0.2% |
| | Water | qs 100% |

Procedure:

Each phase $a_1$ or $a_2$ was prepared by homogenization of the various constituents at 75° C. Each phase $b_1$ or $b_2$ was added, respectively, to phase $a_1$ or $a_2$ at a temperature of 75° C. The mixture was cooled to 25° C.

Each of these preparations were introduced into one of the compartments of a two-compartment pump-dispenser bottle and was mixed with the other preparation on exiting the pump, which led to the production of a tinted cream.

Component B: Acidic Aqueous Gel

| Phase 1: | Acrylates/$C_{10}$-$C_{30}$ alkyl acrylate crosspolymer | 0.25% |
|---|---|---|
| | Base | 0.15% |
| Phase 2: | Xanthan | 0.3% |
| | Glycerol | 3% |
| | Propylene glycol | 3% |
| | PEG-8 | 3% |
| | Lactic acid | 0.5% |
| | Preserving agent | 0.1% |
| | Water | qs 100% |

Procedure

Phase 1: The carboxylic acid was dispersed in the water and was then neutralized with the base.

Phase 2: The phase was prepared by homogenizing the various constituents. The mixing of phase 1 and phase 2 was then performed. The pH obtained was less than 5.

Component C: Basic Aqueous Solution

| Glycerol | 3% |
|---|---|
| PEG-8 | 3% |
| Triethanolamine | 0.9% |
| Preserving agent | 0.1% |
| Eau de Vichy (Eau de Lucas) | 5% |
| Water | qs 100% |

The triethanolamine may advantageously be replaced with sodium hydroxide.

The composition comprising component ($A_1$) and component ($A_2$) was applied to the skin by means of the pump-dispenser bottle. A uniform color was obtained after about 5 minutes, giving the user a tanned complexion. The color thus obtained was then fixed by applying the acidic gel (B) to the colored area of the skin. After a few hours, according to the wishes of the user, the color was revived (re-established the first shade obtained by applying the composition comprising component ($A_1$) and component ($A_2$) and then (B)) by applying solution (C) optionally followed by applying product (B) to fix the color again.

What is claimed is:

1. A process for coloring a keratin material, comprising applying to the keratin material, in the presence of oxygen,
    at least one component (A) comprising, in a physiologically acceptable medium,
        at least one dye precursor chosen from compounds comprising at least one aromatic ring comprising at least two hydroxyl groups borne by two successive carbon atoms of the at least one aromatic ring, and
        at least one catalytic system comprising at least one first catalyst (1) chosen from Mn(II) and Zn(II) salts and oxides and at least one second catalyst (2) chosen from alkali metal hydrogen carbonates and alkaline-earth metal hydrogen carbonates;
    developing the color to obtain a desired shade,
    applying at least one component (B) comprising at least one acidic composition to the keratin material to fix the shade;
    applying at least one component (C) comprising at least one alkaline composition to the keratin material to increase the intensity of the color or to modify the shade; and
    optionally fixing the new color or shade obtained by applying a new application of at least one component (B) comprising at least one acidic composition to the keratin material.

2. The process according to claim 1, wherein the oxygen is atmospheric oxygen.

3. A process for coloring a keratin material, comprising:
    applying to the keratin material at least one component ($A_1$) comprising, in a physiologically acceptable medium,
        at least one dye precursor chosen from compounds comprising at least one aromatic ring comprising at least two hydroxyl groups borne by two successive carbon atoms of the at least one aromatic ring and
        at least one catalyst system comprising either at least one first catalyst (1) chosen from Mn(II) and Zn(II) salts and oxides or at least one second catalyst (2) chosen from alkali metal hydrogen carbonates and alkaline-earth metal hydrogen carbonates;
    revealing the color in the presence of oxygen by applying at least one component ($A_2$) comprising the other of the at least one first catalyst (1) and the at least one second catalyst (2) not present in the at least one component ($A_1$),
    developing the color to obtain the desired shade,
    applying at least one component (B) comprising at least one acidic composition to the keratin material to fix the shade;
    optionally applying at least one component (C) comprising at least one alkaline composition to the keratin material to increase the intensity of the color or to modify the shade; and
    optionally fixing the new color or shade obtained by applying a new application of at least one component (B) comprising at least one acidic composition to the keratin material.

4. The process according to claim 3, wherein the oxygen is atmospheric oxygen.

5. A process for coloring a keratin material comprising applying to a keratin material, in the presence of oxygen,
    at least one component (A) comprising, in a physiologically acceptable medium,
        at least one dye precursor chosen from compounds comprising at least one aromatic ring comprising at least two hydroxyl groups borne by two successive carbon atoms of the at least one aromatic ring, and
        at least one catalytic system comprising at least one first catalyst (1) chosen from Mn(II) and Zn(II) salts and oxides and at least one second catalyst (2) chosen from alkali metal hydrogen carbonates and alkaline-earth metal hydrogen carbonates;
    applying at least one component (C) comprising at least one alkaline composition to the keratin material to increase the intensity of the color or to modify the shade; and
    fixing the new color or shade obtained by applying at least one component (B) comprising at least one acidic composition to the keratin material.

6. The process according to claim 5, wherein the oxygen is atmospheric oxygen.

7. A process for coloring a keratin material, comprising
    applying to the keratin material, at least one component ($A_1$) comprising, in a physiologically acceptable medium,
        at least one dye precursor chosen from compounds comprising at least one aromatic ring comprising at least two hydroxyl groups borne by two successive carbon atoms of the at least one aromatic ring and
        at least one catalyst system comprising either at least one first catalyst (1) chosen from Mn(II) and Zn(II) salts and oxides or at least one second catalyst (2) chosen from alkali metal hydrogen carbonates and alkaline-earth metal hydrogen carbonates,
    developing the color in the presence of oxygen by applying at least one component ($A_2$) comprising the other of the at least one first catalyst (1) and the at least one second catalyst (2) not present in the at least one component ($A_1$),
    applying at least one component (C) comprising at least one alkaline composition to the keratin material to increase the intensity of the color or to modify the shade; and
    optionally fixing the new color or shade obtained by applying at least one component (B) comprising at least one acidic composition to the keratin material.

8. The process according to claim 7, wherein the oxygen is atmospheric oxygen.

9. The process according to claim 1, wherein the proportions of the at least one first catalyst (1) to the at least one second catalyst (2) are chosen such that:

$$\frac{[Mn(II)]}{[HCO_3-]} \leq 1 \text{ with } [Mn(II)] \neq 0$$

$$\frac{[Zn(II)]}{[HCO_3-]} \leq 1 \text{ with } [Zn(II)] \neq 0$$

$$\frac{[Mn(II) + Zn(II)]}{[HCO_3-]} \leq 1 \text{ with } [Mn(II)] \text{ and } [Zn(II)] \neq 0$$

wherein [Mn(II)], [Zn(II)] and [$HCO_3^-$] represent, respectively, the molar concentrations of Mn(II), Zn(II) and $HCO_3^-$ in the composition.

10. The process according to claim 9, wherein the ratio $$\frac{[Mn(II)]}{[HCO_3-]}$$

ranges from $10^{-5}$ to $10^{-1}$.

11. The process according to claim 10, wherein the ratio $$\frac{[Mn(II)]}{[HCO_3-]}$$

ranges from $10^{-3}$ to $10^{-2}$.

12. The process according to claim 11, wherein the ratio $$\frac{[Mn(II)]}{[HCO_3-]}$$

is about $5 \times 10^{-3}$.

13. The process according to claim 9, wherein the ratio $$\frac{[Zn(II)]}{[HCO_3-]}$$

ranges from $10^{-4}$ to <1.

14. The process according to claim 13, wherein the ratio $$\frac{[Zn(II)]}{[HCO_3-]}$$

ranges from $10^{-3}$ to <1.

15. The process according to claim 14, wherein the ratio $$\frac{[Zn(II)]}{[HCO_3-]}$$

is about $5 \times 10^{-1}$.

16. The process according to claim 9, wherein the ratio $$\frac{[Mn(II) + Zn(II)]}{[HCO_3-]}$$

ranges from $10^{-5}$ to $10^{-1}$.

17. The process according to claim 16, wherein the ratio $$\frac{[Mn(II) + Zn(II)]}{[HCO_3-]}$$

ranges from $10^{-3}$ to $10^{-2}$.

18. The process according to claim 1, wherein the Mn(II) and Zn(II) salts are chosen from at least one of chloride, fluoride, iodide, sulphate, phosphate, nitrate, perchlorate, and carboxylic acid salts.

19. The process according to claim 18, wherein the Mn(II) and/or Zn(II) salts are chloride salts.

20. The process according to claim 18, wherein the carboxylic acid salts are chosen from hydroxylated carboxylic acid salts.

21. The process according to claim 20, wherein the hydroxylated carboxylic acid salt is gluconate.

22. The process according to claim 1, wherein the alkali metal hydrogen carbonates and alkaline earth metal hydrogen carbonates are chosen from at least one of sodium hydrogen carbonate, potassium hydrogen carbonate, magnesium hydrogen carbonate, and calcium hydrogen carbonate.

23. The process according to claim 1, wherein the at least one aromatic ring of the at least one dye precursor is chosen from a benzene ring and fused aromatic rings.

24. The process according to claim 23, wherein the at least one dye precursor is chosen from compounds of the following formula:

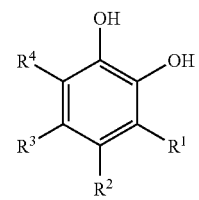

(I)

wherein:
$R^1, R^2, R^3, R^4$, which may be identical or different, are each chosen from a hydrogen atom, halogen atoms, hydroxyl groups, carboxyl groups, alkylcarboxylate groups, optionally substituted amino groups, optionally substituted linear or branched alkyl groups, optionally substituted linear or branched alkenyl groups, optionally substituted cycloalkyl, alkoxy, alkoxyalkyl and alkoxyaryl radicals, the aryl group being optionally substituted, aryl and substituted aryl radicals, optionally substituted heterocyclic radicals, and radicals optionally comprising at least one silicon atom, wherein two of the substituents chosen from $R^1, R^2, R^3$, and $R^4$ together form at least one ring chosen from saturated and unsaturated rings optionally comprising at least one heteroatom and optionally fused with at least one ring chosen from saturated and unsaturated rings optionally comprising at least one heteroatom.

25. The process according to claim 1, wherein the at least one dye precursor is chosen from flavanols, anthocyanidins, anthocyanins, hydroxybenzoates, flavones and iridoids, these compounds optionally being osylated and/or in the form of oligomers, hydroxystilbenes which are optionally osylated, 3,4-dihydroxyphenylalanine, 2,3-dihydroxyphenylalanine, 4,5-dihydroxyphenylalanine, 4,5-dihydroxyindole, 5,6-dihydroxyindole, 6,7-dihydroxyindole, 2,3-dihydroxyindole, dihydroxycinnamates, hydroxycoumarins, hydroxyisocoumarins, hydroxycoumarones, hydroxyisocoumarones, hydroxychalcones, hydroxychromones, anthocyans, quinones and hydroxyxanthones.

26. The process according to claim 1, wherein the at least one dye precursor is chosen from extracts of plants, of fruits, of citrus plants, and of vegetables.

27. The process according to claim 26, wherein the at least one dye precursor is chosen from extracts of tea, of grape, of apple, of cocoa, of sorghum, of banana, and of potato.

28. The process according to claim 1, wherein the at least one dye precursor is present in the at least one component (A) in an amount of at least 10 micromol per milliliter of component (A).

29. The process according to claim 1, wherein the physiologically acceptable medium is a solubilizing medium for the at least one dye precursor.

30. The process according to claim 29, wherein the physiologically acceptable medium is a solubilizing medium with bacteriostatic properties.

31. The process according to claim 1, wherein the physiologically acceptable medium comprises at least one solvent for the at least one dye precursor.

32. The process according to claim 31, wherein the solvent is chosen from water, alcohols, ethers, dimethyl sulphoxide, N-methylpyrrolidone, and acetone.

33. The process according to claim 32, wherein the alcohols are chosen from alkanols and alkanediols.

34. The process according to claim 32, wherein the at least one solvent is a water/alcohol mixture.

35. The process according to claim 34, wherein the alcohol is present in an amount up to 80% by weight, relative to the total weight of the water/alcohol mixture.

36. The process according to claim 35, wherein the alcohol is present in an amount ranging from 1% to 50% by weight, relative to the total weight of the water/alcohol mixture.

37. The process according to claim 36, wherein the alcohol is present in an amount ranging from 5% to 20% by weight, relative to the total weight of the water/alcohol mixture.

38. The process according to claim 1, wherein the at least one component (A) is free of any agent for chelating the Mn(II) and/or Zn(II) salts.

39. The process according to claim 1, wherein the at least one component (A) comprises no propigmenting enzymes.

40. The process according to claim 1, wherein the at least one component (A) is independently chosen from creams, milks, gels, cream-gels, lotions, powders, and solid blocks.

41. The process according to claim 1, wherein the at least one component (A) is packaged in a one-compartment device comprising the at least one dye precursor and at least one catalytic system.

42. The process according to claim 41, wherein the one-compartment device is in a form chosen from an airtight metal tube, an ampule, a sachet, a sealed wipe, an aerosol comprising at least one standard inert propellant gas, a pump device without air intake, and a solid block.

43. The process according to claim 3, wherein the components ($A_1$) and ($A_2$) are packaged in the form of a kit comprising two separate containers; the first container comprising the component ($A_1$) comprising the at least one dye precursor and one of the at least one catalyst (1) and the at least one catalyst (2), the second container comprising the component ($A_2$) comprising the other of the at least one catalyst (1) and the at least one catalyst (2) not present in the component ($A_1$), wherein the components ($A_1$) and ($A_2$) are mixed together or applied successively at the time of use.

44. The process according to claim 43, wherein each container, which may be identical or different, is packaged in a device chosen from an airtight metal tube, an ampule, a sachet, a sealed wipe, an aerosol comprising at least one standard inert propellant gas, a pump device without air intake, and a solid block.

45. The process according to claim 43, wherein the kit comprising two separate containers is a two-compartment aerosol device comprising, respectively, the components ($A_1$) and ($A_2$) and with which at least one distribution orifice may be selectively placed in communication; depending on the configuration of the device, the components ($A_1$) and ($A_2$) may be distributed simultaneously or successively at the time of use.

46. The process according to claim 43, wherein the device is a system comprising two compartments each equipped with a pump without air intake, the first compartment comprising the component ($A_1$), and the other compartment comprising the component ($A_2$); depending on the configuration of the device, the components ($A_1$) and ($A_2$) may be distributed simultaneously or successively at the time of use.

47. The process according to claim 1, wherein the at least one component (A) is in the form of solid blocks that may be disintegrated in water.

48. The process according to claim 1, wherein the component (B) comprises an aqueous composition comprising at least one acid chosen from mineral and organic acid.

49. The process according to claim 48, wherein the pH of the component (B) ranges from 1 to 6.

50. The process according to claim 49, wherein the pH of the component (B) ranges from 2 to 5.

51. The process according to claim 48, wherein the mineral acids are chosen from at least one of hydrochloric acid (HCl) and phosphoric acid ($H_3PO_4$).

52. The process according to claim 48, wherein the component comprises naturally acidic water.

53. The process according to claim 48, wherein the organic acids are chosen from at least one of acetic acid, α-hydroxy acids, β-hydroxy acids and α- and β-keto acids.

54. The process according to claim 48, wherein the organic acids are chosen from at least one of glycolic acid, lactic acid, malic acid, tartaric acid, citric acid, mandelic acid and salicylic acid, and alkyl and alkoxy derivatives thereof.

55. The process according to claim 54, wherein the organic acids are chosen from at least one of lactic acid, glycolic acid, and citric acid.

56. The process according to claim 1, wherein the component (B) is packaged in a form chosen from a bottle, a jar, a tube, a sachet, a wipe, an aerosol, a spray, and a solid stick.

57. The process according to claim 1, wherein the component (C) comprises an aqueous composition comprising at least one base chosen from mineral bases and organic bases.

58. The process according to claim 57, wherein the pH of the component (C) ranges from 7 to 12.

59. The process according to claim 58, wherein the pH of the component (C) ranges from 8 to 10.

60. The process according to claim 57, wherein the mineral bases are chosen from at least one of alkali metal and alkaline-earth metal salts and alkali metal and alkaline-earth metal hydrogen carbonates.

61. The process according to claim 57, wherein the component (C) is naturally alkaline mineral water.

62. The process according to claim 57, wherein the organic bases are chosen from alkanolamines.

63. The process according to claim 1, wherein the component (C) is packaged in a form chosen from a bottle, a jar, a tube, a sachet, a wipe, an aerosol, a spray, and a solid stick.

* * * * *